US006657206B2

(12) United States Patent
Keogh et al.

(10) Patent No.: US 6,657,206 B2
(45) Date of Patent: Dec. 2, 2003

(54) ULTRAVIOLET LAMP SYSTEM AND METHODS

(75) Inventors: Patrick Gerard Keogh, Berkshire (GB); James W. Schmitkons, Lorain, OH (US)

(73) Assignee: Nordson Corporation, Westlake, OH (US)

( * ) Notice: Subject to any disclaimer, the term of this patent is extended or adjusted under 35 U.S.C. 154(b) by 282 days.

(21) Appl. No.: 09/826,028

(22) Filed: Apr. 4, 2001

(65) Prior Publication Data

US 2002/0050575 A1 May 2, 2002

Related U.S. Application Data

(63) Continuation-in-part of application No. 09/702,519, filed on Oct. 31, 2000.

(51) Int. Cl.[7] .................................................. A61N 5/00
(52) U.S. Cl. ................................ 250/492.1; 250/504 R
(58) Field of Search ......................... 250/492.1, 492.22, 250/493.1, 503.1, 504 R

(56) References Cited

U.S. PATENT DOCUMENTS

| | | | | | |
|---|---|---|---|---|---|
| 3,872,349 A | * | 3/1975 | Spero et al. | .................. | 315/39 |
| 4,042,850 A | | 8/1977 | Ury et al. | ..................... | 315/39 |
| 4,535,753 A | | 8/1985 | Zayauskas | .................. | 126/274 |
| 4,591,724 A | * | 5/1986 | Fuse et al. | ............... | 250/492.1 |
| 4,710,638 A | * | 12/1987 | Wood | ...................... | 250/492.1 |
| 4,928,040 A | | 5/1990 | Uesaki | ....................... | 315/248 |
| 4,990,789 A | | 2/1991 | Uesaki | ....................... | 250/504 |
| 5,136,491 A | | 8/1992 | Kano | ......................... | 362/346 |
| 6,345,149 B1 | * | 2/2002 | Ervin et al. | ................ | 392/417 |

FOREIGN PATENT DOCUMENTS

| | | |
|---|---|---|
| FR | 91-03873 | 10/1992 |

* cited by examiner

*Primary Examiner*—John R. Lee
*Assistant Examiner*—Christopher M. Kalivoda
(74) *Attorney, Agent, or Firm*—Wood, Herron & Evans, L.L.P.

(57) ABSTRACT

An ultraviolet radiation generating system and methods is disclosed for treating a coating on a substrate, such as a coating on a fiber optic cable. The system comprises a microwave chamber having one or more ports capable of permitting the substrate to travel within or through a processing space of the microwave chamber. A microwave generator is coupled to the microwave chamber for exciting a longitudinally-extending plasma lamp mounted within the processing space of the microwave chamber. The plasma lamp emits ultraviolet radiation for irradiating the substrate in the processing space. A pair of reflectors are mounted within the processing space of the microwave chamber. The reflectors are capable of reflecting a significant portion of the ultraviolet radiation to irradiate the backside of the substrate in a surrounding and uniform fashion. When the system is operating, the microwave chamber is substantially closed to emission of microwave energy and ultraviolet radiation.

15 Claims, 4 Drawing Sheets

ULTRAVIOLET LAMP SYSTEM AND METHODS

CROSS-REFERENCE TO RELATED APPLICATIONS

This application is a Continuation-in-Part of commonly assigned, co-pending application Ser. No. 09/702,519, filed Oct. 31, 2000 and entitled ULTRAVIOLET LAMP SYSTEM AND METHODS, naming Patrick G. Keogh and James W. Schmitkons as inventors, the disclosure of which is hereby incorporated by reference herein in its entirety.

FIELD OF THE INVENTION

The present invention relates generally to ultraviolet lamp systems and, more particularly, to microwave-excited ultraviolet lamp systems configured to irradiate a substrate with ultraviolet radiation.

BACKGROUND OF THE INVENTION

Ultraviolet lamp systems are commonly used for heating and curing materials such as adhesives, sealants, inks, and coatings. Certain ultraviolet lamp systems have electrodeless light sources and operate by exciting an electrodeless plasma lamp with either radiofrequency energy or microwave energy. In an electrodeless ultraviolet lamp system that relies upon excitation with microwave energy, the electrodeless plasma lamp is mounted within a metallic microwave cavity or chamber. One or more microwave generators are coupled via waveguides with the interior of the microwave chamber. The microwave generators supply microwave energy to initiate and sustain a plasma from a gas mixture enclosed in the plasma lamp. The plasma emits a characteristic spectrum of electromagnetic radiation strongly weighted with spectral lines or photons having ultraviolet and infrared wavelengths. To irradiate a substrate, the radiation is directed from the microwave chamber through a chamber outlet to an external location. The chamber outlet is capable of blocking emission of microwave energy but allows electromagnetic radiation to be transmitted outside the microwave chamber. A fine-meshed metal screen covers the chamber outlet of many conventional ultraviolet lamp systems. The openings in the metal screen transmit electromagnetic radiation for irradiating a substrate positioned outside the microwave chamber, yet substantially block the emission of microwave energy.

The electrodeless plasma lamp emits a characteristic spectrum isotropically outward along its cylindrical length. Part of the emitted radiation moves directly from the plasma lamp toward the substrate without reflection. However, a significant portion of the emitted radiation must undergo one or more reflections to reach the substrate. To capture this indirect radiation, a reflector can be provided that is mounted within the microwave chamber in which the plasma lamp is positioned. The reflector includes surfaces capable of redirecting incident radiation in a predetermined pattern toward the chamber outlet and to the substrate positioned outside the microwave chamber.

A major shortcoming of conventional systems is the inability to accurately predict the focal point or focal plane outside the microwave chamber at which the reflected ultraviolet radiation will be delivered. Another shortcoming is the reflector of the lamp system cannot be easily modified to adjust the focal point or focal plane, if known, so that the substrate can be repositioned relative to the lamp system. Further, the inability to accurately predict the focal point or focal plane limits the ability to mass produce lamp systems capable of delivering predictable radiation patterns to a substrate. A further limitation is that conventional ultraviolet lamp systems are designed to irradiate a flat surface on large-area substrates and cannot be easily adapted to uniformly irradiate substrates in a surrounding fashion. For example, conventional ultraviolet lamp systems cannot uniformly irradiate the entire circumference of round substrates.

If the plasma lamp is considered a line source of radiation, the intensity of ultraviolet radiation striking the substrate is inversely proportional to the separation between the plasma lamp and the substrate. As a result, the ultraviolet radiation is significantly attenuated when traveling from the plasma lamp on the interior of the microwave chamber to the substrate positioned outside the microwave chamber. To compensate for this loss in intensity, the microwave power must be elevated to increase the output of the plasma lamp. However, the amount of infrared radiation will likewise increase with the output of the plasma lamp. The excess infrared energy heats the substrate, the microwave chamber, and the plasma lamp. The elevation in temperature associated with the excess infrared energy can significantly reduce the lifetime of the plasma lamp and can produce additional undesirable effects.

Thus, a microwave-excited ultraviolet lamp system is needed with a configuration capable of uniformly irradiating a substrate positioned within the microwave chamber with ultraviolet radiation and that can do so without emitting significant amounts of microwave energy.

SUMMARY OF THE INVENTION

The present invention overcomes the foregoing and other deficiencies of conventional microwave-excited ultraviolet lamp systems. While the invention will be described in connection with certain embodiments, the invention is not limited to these embodiments. On the contrary, the invention includes all alternatives, modifications and equivalents as may be included within the spirit and scope of the present invention.

According to the present invention, an ultraviolet radiation generating system for treating a coating on a substrate, such as a coating on a cable or, more specifically, a coating on a fiber optic cable, comprises a microwave chamber having an inlet port capable of permitting the cable to be positioned within or to travel within a processing space of the microwave chamber. During operation, the microwave chamber is substantially closed to emission of microwave energy and the emission of ultraviolet radiation. A microwave generator is coupled to the microwave chamber for exciting a longitudinally-extending plasma lamp mounted within the processing space of the microwave chamber. The plasma lamp emits ultraviolet radiation for irradiating the substrate. A first portion of the ultraviolet radiation directly irradiates the frontside of the substrate. Mounted within the microwave chamber is a pair of reflectors which substantially surround the processing space. The reflectors are capable of reflecting a portion of the ultraviolet radiation for indirectly irradiating the backside of the substrate with reflected ultraviolet radiation.

In certain embodiments, the microwave chamber may further include an outlet port so that the substrate travels between the inlet and outlet ports through the microwave chamber at least partially within the processing space. In other embodiments, the lamp system may also include an ultraviolet-transmissive conduit positioned within the microwave chamber generally between the inlet and outlet ports. The conduit encloses the substrate when it is positioned within the processing space of the microwave chamber. In still other embodiments, the lamp system may also include microwave chokes which are capable of reducing the emission of microwave energy from the inlet and outlet ports.

According to methods of the present invention, a substrate is positionable within a processing space of a microwave and a plasma lamp is excited with microwave energy to emit ultraviolet radiation for irradiating the substrate. While the substrate is positioned within or traveling through the processing space, the frontside of the substrate is irradiated with direct ultraviolet radiation emitted from the plasma lamp and the backside of the substrate is irradiated with indirect ultraviolet radiation emanating from the plasma lamp which is reflected from a pair of reflectors. The substrate is removed from the processing space after irradiating.

The present invention permits the substrate to be positioned directly within the microwave chamber for treatment with ultraviolet radiation. As a result, the chamber may be completely sealed to prohibit the emission of microwave energy and to eliminate the need to emit ultraviolet radiation from the microwave chamber. Because the substrate, the plasma lamp, and the reflector have well-defined relative positions within the microwave chamber, the plasma lamp and reflector can be precisely located relative to the substrate for purposes of providing a predictable, reproducible and substantially uniform pattern of radiation at and distributed about or surrounding the substrate. Furthermore, because the substrate is positioned within the microwave chamber and because the ultraviolet radiation does not have to be transmitted through a screen to a location outside of the microwave chamber, a greater intensity of ultraviolet radiation per unit measure of microwave energy can be delivered to the substrate. As a result, the microwave energy can be reduced to deliver a given intensity of ultraviolet radiation to the substrate or the ultraviolet intensity can be optimized for improving the treatment throughput of the lamp system.

The above and other advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF PREFERRED EMBODIMENTS

The present invention relates to microwave-excited ultraviolet lamp systems configured to uniformly irradiate with ultraviolet radiation a substrate positioned within or traveling within a processing space of the microwave chamber. According to present invention, the lamp system is configured such that the substrate is capable of being positioned in the processing space near a microwave-excited plasma lamp, thereby increasing the intensity of the ultraviolet radiation irradiating the substrate. Further, the positioning of the substrate within the processing space eliminates the need to transmit the ultraviolet radiation outside of the microwave chamber for treating the substrate. Further, the present invention incorporates a reflector or a pair of reflectors that, along with the direct ultraviolet radiation from the plasma lamp, participate in providing a substantially uniformly irradiance of ultraviolet radiation in a surrounding relationship relative to, or about the circumference of, the substrate. Further, the present invention isolates the substrate with an ultraviolet-transmissive conduit such that fragile substrates can be accommodated and yet a sufficient air flow can be provided to cool the microwave generators and the plasma lamp of the system. Further, the present invention permits the substrate to enter the microwave chamber and to travel within or be positioned within the processing space without substantial microwave leakage from the chamber. Further, the reflector or reflectors, the substrate, and the plasma lamp are positioned within the processing space of the microwave chamber so as to provide a precise, reproducible and substantially uniform pattern of ultraviolet radiation that surrounds the substrate. As used herein, treatment encompasses curing, heating, or any other process that alters a physical property of a substrate or a coating on a substrate as a result of exposure to ultraviolet radiation.

Figure 1:
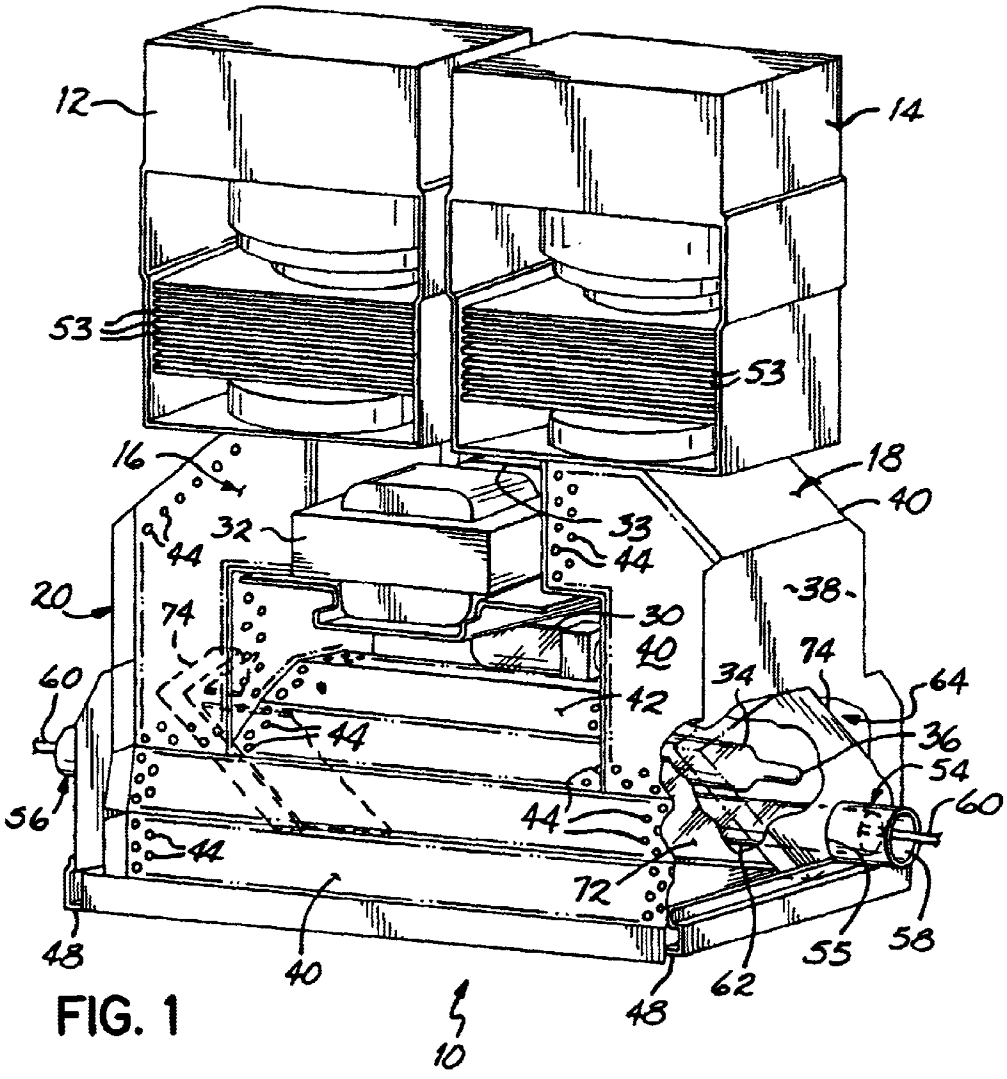
FIG. 1 is a perspective side view of an ultraviolet lamp system of the present invention.
Figure 2:
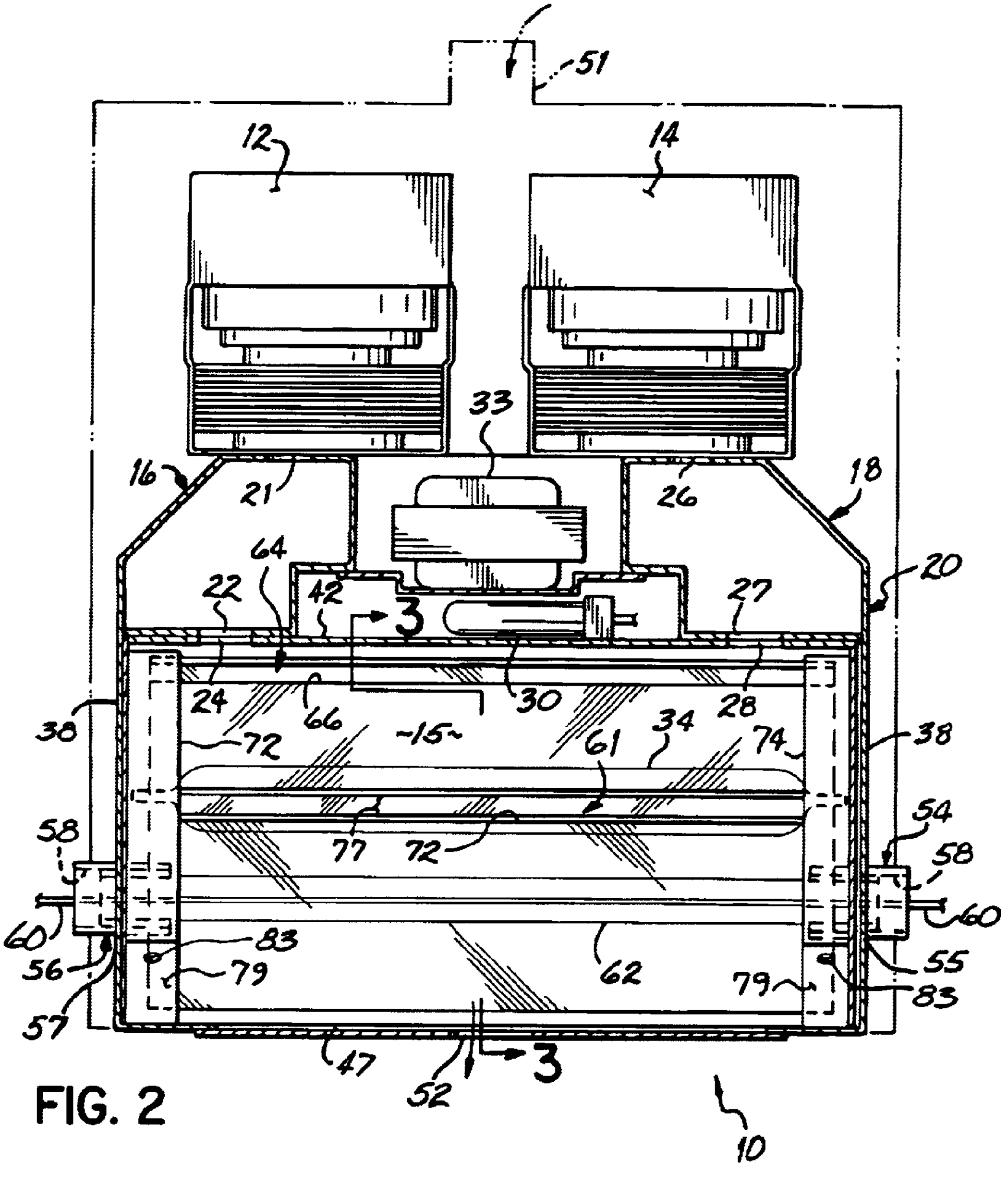
FIG. 2 is a partial longitudinal cross-sectional view of an ultraviolet lamp system taken along line 2—2 of FIG. 1.

With reference to FIGS. 1 and 2, a microwave-excited ultraviolet lamp system of the present invention is indicated generally by reference numeral 10. Lamp system 10 includes a pair of microwave generators 12 and 14, illustrated as magnetrons, mechanically mounted by a respective one of a pair longitudinally-spaced waveguides 16 and 18 to a longitudinally-extending microwave chamber, indicated generally by reference numeral 20. A pair of transformers 32 and 33 (FIG. 2 shows only transformer 33) are electrically coupled to a respective one of the microwave generators 12 and 14 for energizing filaments of the microwave generators 12 and 14 as understood by those of ordinary skill in the art. To prevent cross-coupling when the lamp system 10 is operating, the operating frequencies of the two microwave generators 12 and 14 should be offset by a small amount. By way of specific example but not limitation, the two microwave generators 12 and 14 may operate at respective frequencies of about 2470 MHz and about 2445 MHz, which represents a frequency offset of 25 MHz, and may have individual power ratings of about 3 kW.

While a pair of microwave generators 12 and 14 is illustrated and described herein, the lamp system 10 may include only a single microwave generator without departing from the spirit and scope of the present invention. Waveguide 16 includes an inlet port 21 coupled with microwave generator 12 and an outlet port 22 which is aligned and coupled for microwave transmission with an opening 24 provided in the microwave chamber 20. Similarly, waveguide 18 includes an inlet port 26 coupled with microwave generator 14 and an outlet port 27 which is aligned and coupled for microwave transmission with an opening 28 provided in the microwave chamber 20. Microwave energy from the microwave generators 12 and 14 is directed via waveguides 16 and 18 to an interior space 15 of the microwave chamber 20 through the openings 24 and 28. Microwave energy is deposited with a three-dimensional density distribution within the microwave chamber 20 as understood by those of ordinary skill in the art.

A plasma lamp 34 is positioned longitudinally within the microwave chamber 20. Opposite ends 36 of plasma lamp 34 are supported within the microwave chamber 20 as understood by those of ordinary skill in the art. Plasma lamp 34 comprises a hermetically sealed, longitudinally-extending envelope or tube filled with a gas mixture. Plasma lamp 34 does not require either electrical connections or electrodes for its operation. The plasma lamp 34 is formed of an ultraviolet-transmissive material that is an electrical insulator, such as vitreous silica or quartz, so that the plasma lamp 34 is electrically isolated from other structures in the microwave chamber 20. Microwave energy provided by the microwave generators 12 and 14 guides excited atoms in the gas mixture within plasma lamp 34 to initiate and, thereafter, sustain the plasma therein. A starter bulb 30 is provided to assist in initiating a plasma within plasma lamp 34 as understood by those of ordinary skill in the art. By adjusting the shape of microwave chamber 20 and the power level of microwave generators 12 and 14, the density distribution of the microwave energy is selected to excite atoms in the gas mixture along the entire longitudinal dimension of the plasma lamp 34. Once the plasma is initiated, the intensity of the radiation output by the plasma lamp 34 depends upon the microwave power provided to microwave chamber 20 by microwave generators 12 and 14.

The gas mixture inside plasma lamp 34 has an elemental composition selected to produce photons having a predetermined distribution of wavelengths of radiation when the gas atoms are excited to a plasma state. For ultraviolet treating applications, the gas mixture may comprise a mercury vapor and an inert gas, such as argon, and may include trace amounts of one or more elements such as iron, gallium, or indium. The mercury vapor is provided by the vaporization of a small quantity of mercury that is solid at room temperature. The spectrum of radiation output by a plasma excited from such a gas mixture includes highly intense ultraviolet and infrared spectral components. As used herein, radiation is defined as photons having wavelengths ranging between about 200 nm to about 2000 nm, ultraviolet radiation is defined as photons having wavelengths ranging between about 200 nm to about 400 nm, and infrared radiation is defined as photons having wavelengths ranging between about 750 nm to about 2000 nm.

As best understood with reference to FIG. 1, microwave chamber 20 includes a pair of generally vertical opposite end walls 38 and a pair of generally vertical opposite side walls 40 extending longitudinally between the end walls 38 and on opposite sides of the plasma lamp 34. A segmented, domed wall 42 connects intermediate portions of the side walls 40 between openings 24 and 28. Walls 38, 40, and 42 are each perforated with a plurality of openings 44 that permit the free flow of air. It is understood that the walls of microwave chamber 20 can be configured differently without departing from the spirit and scope of the present invention. In particular, the configuration of the domed wall 42 can be varied to alter or tune the density distribution of microwave energy within microwave chamber 20. Microwave chamber 20 is constructed of a suitable metal, such as a stainless steel, that confines the microwave energy to the interior space 15 of the microwave chamber 20.

Figure 3:
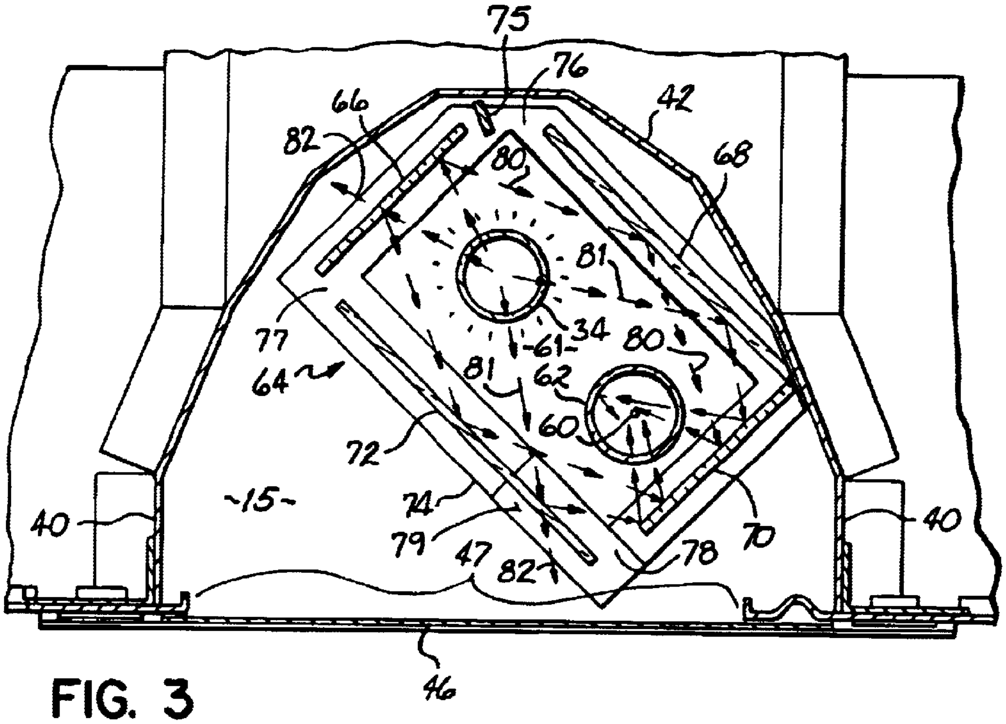
FIG. 3 is a cross-sectional view of the ultraviolet lamp system of FIG. 1 taken along line 3—3 of FIG. 2, showing one embodiment of a reflector for use in the lamp system of FIG. 1.

As best shown in FIG. 3, a cover 46 is mounted to a pair of generally horizontal flanges 48 that extend inwardly from the chamber side walls 40. Cover 46 is removable to reveal an access opening 47 for entry into interior space 15 of the microwave chamber 20. Interior space 15 must be accessed for maintenance purposes, such as servicing or replacing plasma lamp 34 or other objects within the interior space 15 of the microwave chamber 20. Cover 46 has a sealing engagement with access opening 47 that prevents significant amounts of either radiation or microwave energy from being emitted through access opening 47.

With reference to FIG. 2, lamp system 10 is mounted within an enclosure 50, shown in phantom, having a configuration as recognized by those of ordinary skill in the art. The housing 50 includes an air inlet 51 and an air outlet 52 provided in cover 46. A flow of a pressurized gas, such as air, into air inlet 51 is used to regulate the operating temperature of the microwave generators 12 and 14 and the operating temperature of the plasma lamp 34. Microwave generators 12 and 14 each include a plurality of circumferential fins 53. The fins 53 are operable for increasing the efficiency for conducting heat away from the microwave generators 12 and 14 and enhance the available surface area for convective cooling by the flow of air. A fan (not shown) is generally provided as a means for forcing a pressurized flow of air into enclosure 50, over microwave generators 12 and 14, through openings 44 into the microwave chamber 20, and out of enclosure 50 through outlet 52. The pressurized flow of air provides a constant exchange of cool air for heated air within the enclosure 50 and reduces maintenance caused by overheated components. Those skilled in the art would recognize that microwave-excited ultraviolet lamp systems, such as lamp system 10, generate significant amounts of heat that must be eliminated to avoid unacceptably high operating temperatures.

A microwave choke 54 is attached to an inlet port 55 provided in one of the end walls 38 of the microwave chamber 20. A microwave choke 56 is attached to an outlet port 57 provided in the opposite end wall 38. The ports 55 and 57 and the interior passageways 58 of microwave chokes 54, 56 are gene rally aligned longitudinally. Microwave chokes 54 and 56 are hollow, tubular members with a length and diameter chosen, as would be familiar to those of ordinary skill in the art, for preventing a significant amount of microwave energy from leaking outwardly from the interior space 15 of the microwave chamber 20 through ports 55 and 57. By way of example, and not by way of limitation, microwave chokes 54 and 56 may have a length of about 1 inch and an inner diameter of about 0.75 inches.

Microwave chokes 54 and 56 are attached flush with the ports 55 and 57, respectively, such that no portion of either microwave choke 54 and 56 protrudes a significant distance into the interior space 15 of the microwave chamber 20. Suitable microwave chokes 54 and 56 are constructed of a metal alloy, such as a stainless steel, and include, but are not limited to, waveguide chokes, quarter-wave stub chokes, or corrugated chokes in combination with a resistive choke. In certain embodiments of the present invention, microwave chokes 54 and 56 may be omitted from ports 55 and 57 without departing from the spirit and scope of the present invention.

Lamp system 10 is used for the treatment of a non-conductive substrate 60 which is at least partially covered by a coating or surface layer sensitive to treatment by ultraviolet radiation, such as an ultraviolet-curable coating. Substrate 60 may comprise one or more cables or ribbons which are at least partially covered by a coating or surface layer sensitive to treatment by ultraviolet radiation or, more specifically, one or more fiber optic cables or ribbons which are at least partially covered by a coating or surface layer sensitive to treatment by ultraviolet radiation. Multiple cables or ribbons would be arranged accordingly within the microwave chamber 20 to permit simultaneous treatment.

Substrate 60 travels within or through the interior space 15 via inlet port 55 and outlet port 57 of the microwave chamber 20. Those of ordinary skill will appreciate that substrate 60 may both enter and exit the interior space 15 through one of either the inlet port 55 or the outlet port 57 such that microwave chamber 20 can include only one of inlet port 55 or outlet port 57 without departing from the spirit and scope of the present invention. During transfer within or through the interior space 15 of the microwave chamber 20, the substrate 60 is continuously irradiated with ultraviolet radiation while positioned in a longitudinally-extending processing space 61. Processing space 61 comprises a portion of the interior space 15 having an irradiance or flux density of ultraviolet radiation. Because substrate 60 is positioned directly within the processing space 61 of the microwave chamber 20, the separation distance between the plasma bulb 34 and the substrate 60 is minimized. Because the intensity of ultraviolet radiation per unit measure of microwave energy delivered to the substrate 60 is optimized by the proximity of the plasma bulb 34 to substrate 60 and by the elimination of the need to transmit the ultraviolet radiation externally of the microwave chamber 20, the microwave generators 12 and 14 can be operated at a reduced power level for exciting plasma lamp 34 to deliver a given intensity of ultraviolet energy. Alternatively, the intensity of the ultraviolet radiation can be optimized such that substrate 60 may be transferred through or within the microwave chamber 20 at a higher rate for enhancing the treatment throughput of the lamp system 10.

Because substrate 60 is physically positioned inside the microwave chamber 20 during irradiation, a chamber outlet covered by a metallic mesh screen is not required in one of the walls 38, 40 and 42 of the microwave chamber 20 for transmitting ultraviolet radiation to an externally-positioned substrate and for confining the microwave energy to the interior of the microwave chamber 20. As a result, the microwave chamber 20 is robust, tightly sealed against microwave and ultraviolet leakage, and does require special structure to prevent microwave leakage while irradiating substrate 60 with ultraviolet radiation.

In an aspect of the present invention, the passageways 58 of the inlet port 55 and the outlet port 57 in end walls 38 are generally aligned with an ultraviolet-transmissive conduit 62 positioned within the microwave chamber 20. Conduit 62 extends longitudinally between the end walls 38 and is supported at opposite ends by the interior of passageways 58 of ports 55 and 57. Conduit 62 encloses the substrate 60 during the longitudinal transfer of substrate 60 within the interior space 15 of the microwave chamber 20. Conduit 62 is formed of an electrically-insulating material that is highly transmissive of ultraviolet radiation, such as a quartz or a vitreous silica. Conduit 62 prevents extraneous forces from acting on substrate 60, such as the forced air currents directed into the microwave chamber 20 for cooling the plasma lamp 34. This isolation ability is particularly important if substrate 60 is fragile or otherwise prone to damage. However, the conduit 62 may be omitted, such that substrate 60 is not enclosed while in interior space 15, without departing from the spirit and scope of the present invention.

A longitudinally-extending reflector, indicated generally by reference numeral 64, is positioned within the microwave chamber 20. As best shown in FIG. 3, reflector 64 includes a quartet of longitudinally-extending, rectangular reflector panels 66, 68, 70, and 72. The reflector panels 66, 68, 70, and 72 are mounted in a spaced rectangular arrangement via a pair of brackets 74 attached to opposed end walls 38 of the microwave chamber 20. Brackets 74 are preferably formed of an electrically-insulating material, such as a thermally-stable polymer and, more specifically, a fluoropolymer. Opposite ends of each reflector panel 66, 68, 70, and 72 are received by slots (not shown) in each bracket 74. Reflector panels 66, 68, 70, and 72 have a spaced relationship relative to the plasma lamp 34 and a spaced relationship relative to the ultraviolet-transmissive conduit 62 enclosing substrate 60 such that the portion of interior space 15 between the reflector panels 66, 68, 70, and 72 at least partially defines the processing space 61. Microwave energy provided by microwave generators 12 and 14 is readily transmitted through the reflector panels 66 and 68 for initiating a plasma from the gas mixture in plasma lamp 34 and for sustaining the plasma for the duration of a heating or curing operation. Gaps 76, 77 and 78 are provided between the reflector panels 66, 68, 70, and 72 for permitting a flow of relatively cool air to cool the plasma lamp 34. Diverter baffle 75 is provided to preferentially direct a flow of relatively cool air through gap 76 toward plasma lamp 34.

The reflector panels 66, 68, 70, and 72 are configured with an inclined arrangement relative to the side walls 40 of the microwave chamber 20 so that the plasma lamp 34 can be physically accessed from access opening 47 when cover 46 is removed. As best shown in FIGS. 2 and 3, each bracket 74 includes a removable portion 79 that is attached by fasteners 83. The fasteners 83 are preferably formed of an electrically insulating material, such as a ceramic. To remove reflector panel 72, fasteners 83 are loosened to free the removable portion 79 for detachment from each bracket 74 and reflector panel 72 is slidingly removed from the corresponding slots in brackets 74. With reflector panel 72 removed, the path is unobstructed from the access opening 47 to objects, such as the plasma lamp bulb 34, specifically within the processing space 61 and from the access opening 47 to objects generally within the interior space 15 and within the processing space 61.

The reflector panels 66, 68, 70, and 72 are preferably formed of a radiation-transmissive material, such as a borosilicate glass or, more specifically, a Pyrex® glass. Flat plates of Pyrex® glass suitable for use as reflector panels 66, 68, 70, and 72 are commercially available from Corning Inc. (Corning, N.Y.). Alternatively, reflector panels 66, 68, 70, and 72 may be formed of any material having suitable reflective and thermal properties and, in particular, reflector panels 66, 68, 70, and 72 may be constructed of a metal and need not be radiation-transmissive or infrared-transmissive if integrally formed as a portion of the microwave chamber 20.

For use in the ultraviolet lamp system 10, reflector 64 is operable for at least partially transmitting, reflecting or absorbing photons of specific wavelengths. Specifically, reflector 64 is capable of preferentially reflecting photons of ultraviolet radiation, indicated diagrammatically by arrows 80, from the spectrum of emitted radiation, indicated diagrammatically by arrows 81, emanating from the plasma lamp 34 and preferentially transmitting absorbing photons of infrared radiation, where transmission of infrared radiation is indicated diagrammatically by arrows 82. The preferential transmission and reflection of emitted radiation 81 can be provided by methods known to those of ordinary skill, such as applying a dichroic coating to reflector panels 66, 68, 70, and 72. Due to the nature of the reflections and multiple reflections, the reflector 64 (FIG. 3) provides a flood pattern of ultraviolet radiation 80 reflected to substrate 60, rather than a focused pattern and, in particular, provides a substantially uniform flood pattern of ultraviolet irradiation 80 reflected about the circumference of, or in a surrounding relationship relative to, the substrate 60.

As shown in FIG. 3, a significant portion of the infrared radiation 82 is transmitted through the reflector 64 and channeled to the peripheries of the microwave chamber 20 away from the vicinity of the reflector 64. As a result, the ultraviolet radiation 80 reflected by reflector 64 toward the substrate 60 is not accompanied by a significant intensity of infrared radiation 82. Therefore, substrate 60 remains at a relatively low temperature despite being exposed to a significant intensity of ultraviolet radiation 82. Chamber walls 38, 40 and 42 are capable of absorbing the photons of infrared radiation 82 and dissipating the energy thermally.

Figure 3A:
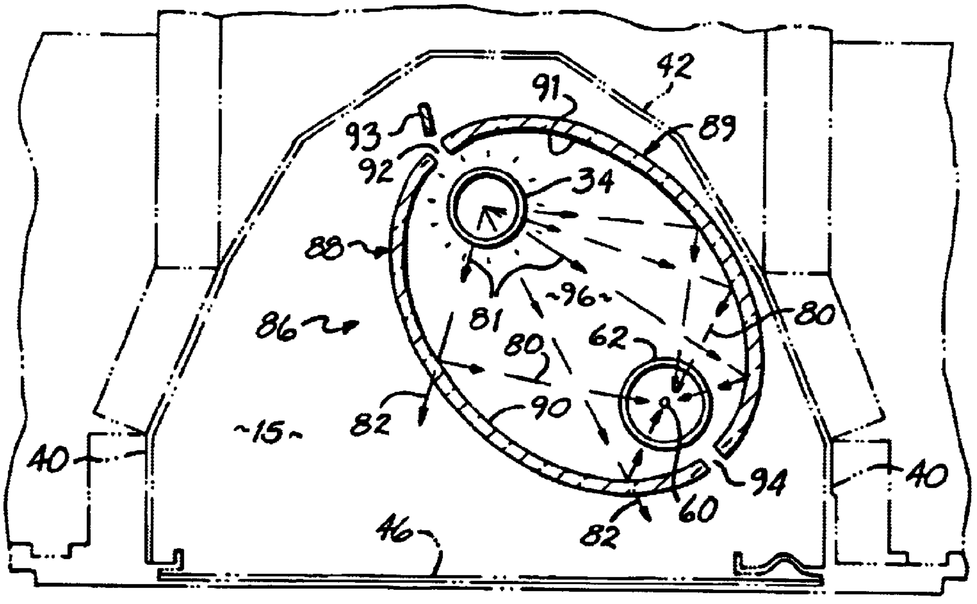
FIG. 3A is a cross-sectional view similar to FIG. 3 of an alternative embodiment of a reflector of the present invention for use in the lamp system of FIG. 1.

Using like reference numerals for like elements discussed with reference to FIGS. 1, 2 and 3, an alternative embodiment of a reflector, indicated generally by reference numeral 86, in accordance with the present invention, is shown in FIG. 3A. Reflector 86 includes a pair of longitudinally extending reflector panels 88 and 89 that are mounted within the microwave chamber 20 as understood by those of ordinary skill in the art on brackets (not shown) similar to brackets 74 (FIGS. 1 and 2). Each reflector panel 88 and 89 has a concave inner surface 90 and 91, respectively, which is generally shaped as a portion of an ellipse having two spaced-foci. The concave inner surfaces 90 and 91 of reflector panels 88 and 89 have an opposing and facing relationship and are positioned with a spaced relationship relative to the plasma lamp 34 and relative to the ultraviolet-transmissive conduit 62 housing the substrate 60. A processing space 96 is at least partially defined between reflector panels 88 and 89 and defines a portion of interior space 15 operable for irradiating substrate 60 with ultraviolet radiation. The reflector panels 88 and 89 are preferably formed of a radiation-transmissive material, such as a borosilicate glass and, more specifically, Pyrex® glass. Gaps 92 and 94 are provided between the reflector panels 88 and 89 for permitting a flow of air to cool the plasma lamp 34. Diverter baffle 93 is provided to preferentially direct the flow of relatively cool air through gap 92 toward plasma lamp 34.

The reflector panels 88 and 89 are arranged such that the respective concave surfaces 90 and 91 generally share common foci to effectively give reflector 86 a full elliptical geometrical shape. Reflector 86 operates in the same manner as discussed above with regard to reflector 64 (FIG. 3) for delivering a relatively uniform irradiance of ultraviolet radiation 80 about the circumference of, or in a surrounding relationship relative to, the substrate 60. However, the ultraviolet radiation is focused about the substrate 60 as compared with the flood of radiation provided by reflector 64 (FIG. 3). Infrared radiation 82 is preferentially transmitted through the reflector 86 and absorbed by the walls 38, 40 and 42 of the microwave cavity 20 for subsequent thermal dissipation. Alternatively, infrared radiation 82 may be absorbed by the reflector 86 and thermally dissipated.

The reflector panels 88 and 89 have a spaced relationship with respect to the plasma lamp 34 and a spaced relationship relative to the substrate 60. The substrate 60 is located near one focus of the ellipse defined by reflector panels 90 and 91, and the plasma lamp 34 is located near the other focus of the ellipse. As a result of the arrangement of plasma lamp 34 and substrate 60, a plurality of substantially focused longitudinal lines of ultraviolet radiation 82 from the plasma lamp 34 is delivered directly and indirectly by reflection from the reflector in a uniform fashion about the circumference of the substrate 60. The lines of ultraviolet radiation 82 are also uniformly delivered along the entire longitudinal dimension of the portion of the substrate 60 positioned within the processing space 96.

A known characteristic of an elliptical reflector is that a ray of radiation emitted from a source positioned at one focus will pass through the other focus after a single reflection. Thus, a light source that approximates a line source, such as plasma lamp 34, that is positioned longitudinally at or near one focus of an elliptical reflector will deliver substantially focused lines of radiation about the circumference of a substrate, such as substrate 60, positioned at or near the second focus. The radiation will be uniformly distributed along the length and about the circumference of the substrate 60 in a surrounding fashion.

Reflector 86 is also positioned relative to the side walls 40 and domed wall 42 of the microwave chamber 20 to permit access through the access opening 47 to the plasma lamp 34 in the processing space 96 and other objects within the interior space 15 and the processing space 96 of the microwave chamber 20. To that end, reflector panel 88 may be removably detached from the brackets (not shown) supporting panel 88 within the microwave chamber 20. After cover 46 is removed, reflector panel 88 is repositioned so that it does not obstruct the path from the access opening 47 in the microwave chamber 20 to the plasma lamp 34.

Figure 3B:
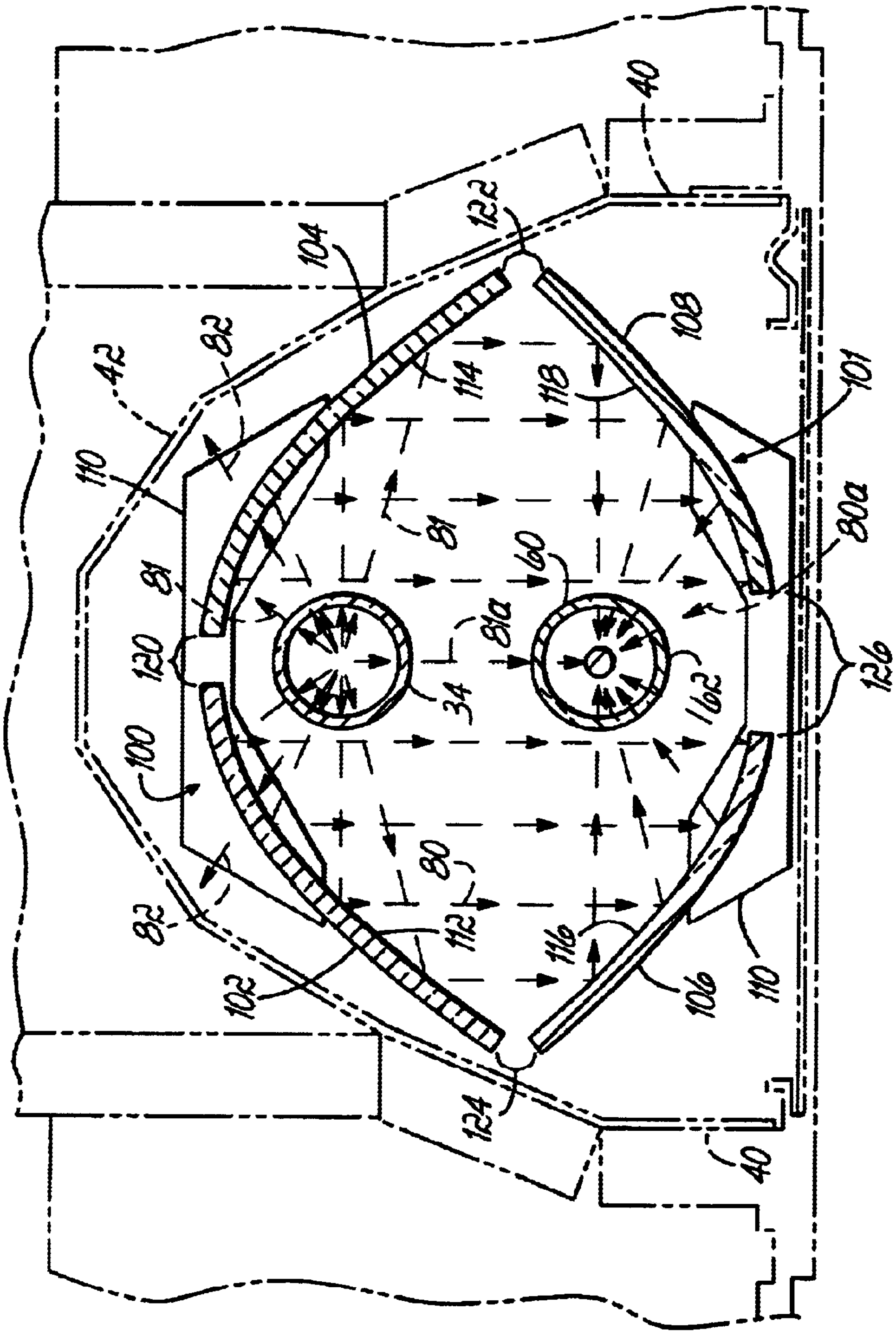
FIG. 3B is a cross-sectional view similar to FIG. 3 of an alternative embodiment of a pair of reflectors according to the present invention for use in the lamp system of FIG. 1.

Using like reference numerals for like elements discussed with reference to FIGS. 1, 2 and 3, a pair of reflectors, indicated generally by reference numerals 100 and 101, in accordance with the present invention, is shown in cross-section in FIG. 3B. Reflector 100 includes reflector panels 102 and 104 extending longitudinally within the microwave chamber 20 between the end walls 38. Similarly, reflector 101 includes reflector panels 106 and 108 which extend longitudinally within the microwave chamber 20 between the end walls 38. The portion of the interior space 15 substantially surrounded by the reflector panels 102–108 at least partially defines the processing space 61 in which the substrate 60 is exposed to ultraviolet radiation. The reflector panels 102–108 are mounted to opposed end walls 38 of the microwave chamber 20 by a pair of longitudinally-spaced brackets 110, of which only one bracket 110 is shown in FIG. 3B. Brackets 110 are formed of an electrically-insulating material, such as a ceramic or a thermally-stable polymer or, more specifically, a fluoropolymer such as those commercially available from E. I. du Pont de Nemours and Company (Wilmington) under the trade name of Teflon®. The brackets 110 are adapted to receive and hold the reflector panels 102–108 in any conventional manner, such as by an adhesive, fasteners, hangers, tabs and slots, or an array of curved grooves inscribed in the respective confronting faces of the brackets 110.

The reflector panels 102–108 are preferably formed of a radiation-transmissive material, such as a borosilicate glass or, more specifically, a Pyrex® glass such as commercially available from Corning Inc. (Corning, N.Y.). Microwave energy provided to microwave chamber 20 by microwave generators 12 and 14 is readily transmitted through the reflector panels 102–108 for initiating a plasma from the gas mixture in plasma lamp 34 and for sustaining the plasma for the duration of the heating or curing operation. Alternatively, reflector panels 102–108 may be formed of any material having suitable reflective and thermal properties. In particular, panels 102–108 may be constructed of a metal and integrally formed as a portion of the microwave chamber or incorporated into or as part of the chamber walls 38, 40 and 42, in which case the panels 102–108 need not transmit radiation of any wavelength.

Reflectors 100 and 101 are adapted to at least partially transmit, reflect or absorb photons of specific wavelengths. In particular and as illustrated in FIG. 3B, reflector panels 102–108 may be capable of preferentially reflecting photons of ultraviolet radiation 80 from the spectrum of emitted radiation 81 emanating from plasma lamp 34 and preferentially transmitting or absorbing photons of infrared radiation 82 therefrom. The preferential transmission, reflection and absorption can be provided by methods familiar to persons of ordinary skill in the art, such as by applying a dichroic coating to reflector panels 102–108 which is configured to selectively transmit infrared radiation 82 from emitted radiation 81 and selectively reflect ultraviolet radiation 81 from emitted radiation 81. This selective transmission directs rays of infrared radiation 82 in optical paths toward the chamber walls 38, 40, 42 and, as a result, the flux of infrared radiation directed toward the substrate 60 is significantly reduced and the amount of infrared radiation irradiating substrate 60 is significantly attenuated.

Reflector panels 102, 104 of reflector 100 have a spaced relationship relative to the plasma lamp 34 and extend longitudinally substantially parallel to lamp 34. Each of the reflector panels 102, 104 has an aspheric concave inner surface 112, 114, respectively, which collectively form, and are arranged in, a common parabolic plane curve or conic section when viewed from a perspective parallel to the longitudinal axis of reflector 100. Each infinitesimal planar cross-section of the reflector panels 102, 104 inherently includes a focal point mathematically representative of the parabolic shape. Because the reflector panels 102, 104 extend longitudinally substantially parallel to the plasma lamp 34, the focal points of the parabolic conic sections collectively form a focal line with which the longitudinal centerline of the plasma lamp 34 is substantially collinear. Axial rays of emitted radiation 81 from the plasma lamp 34, considered as a line source substantially aligned along the focal line, impinge on the inner surfaces 112, 114 of reflector panels 102, 104 and ultraviolet radiation 80 is reflected as substantially-parallel rays having optical paths directed toward the reflector 101.

Reflector panels 106, 108 of reflector 101 have a spaced relationship relative to the ultraviolet-transmissive conduit 62 enclosing substrate 60 and extend longitudinally substantially parallel to conduit 62 and the substrate 60 contained therein. Each of the reflector panels 106, 108 has an aspheric concave inner surface 116, 118, respectively, which collectively form, and are arranged as, a common parabolic plane curve or conic section when viewed from a perspective parallel to the longitudinal axis of reflector 101. Each infinitesimal planar cross-section of the reflector panels 106, 108 inherently includes a focal point mathematically representative of the parabola. Because the reflector panels 106, 108 extend longitudinally substantially parallel to the conduit 62, the focal points of the parabolic conic sections collectively form a focal line with which the longitudinal centerline of the substrate 60 is substantially collinear. A longitudinal axis of the conduit 62 is at least substantially parallel to the focal line and may be collinear therewith. Inner surfaces 116, 118 have a substantially confronting relationship with the inner surfaces 112, 114 of reflector 100. Incident axial, parallel rays of ultraviolet radiation 80, arriving at reflector 101 after reflection from reflector panels 102, 104 of reflector 100, are re-reflected by the inner surfaces 116, 118 as rays of ultraviolet radiation 80*a* that converge or are focused at and about the focal line of the reflector 101.

The substrate 60, positioned longitudinally at or near the focal line, is irradiated by the ultraviolet radiation 80*a* reflected by reflector panels 106, 108. In particular, due to the parabolic shape of the reflector panels 102–108 and their relative arrangement, the non-facing portion or backside of substrate 60, remote from the plasma lamp 34 and shadowed by the facing portion or frontside of substrate 60, is irradiated by the ultraviolet radiation 80*a* reflected by reflector panels 106, 108. Preferably, the irradiation of the backside of substrate 60 by ultraviolet radiation 80*a* is substantially uniform about the circumference and along the length of substrate 60, but the present invention is not so limited. For example, it is understood that the positioning of the plasma lamp 34 and the substrate 60 do not have to precisely coincide with the respective one of the pair of focal lines of reflectors 100 and 101, respectively, and either of the plasma lamp 34 or the substrate 60 can be positioned slightly off-axis without departing from the spirit and scope of the present invention. The frontside of the substrate 60 is irradiated primarily by direct radiation 81*a*, comprising both infrared and ultraviolet wavelengths, emanating from or emitted by the plasma lamp 34.

The separation distance between the reflectors 100 and 101, and more specifically the separation distance between the inner faces 112, 114 of reflector panels 102, 104 and the inner faces 116, 118 of reflector panels 106, 108, can be adjusted within the confines of the microwave chamber 20, provided that the respective focal lines remain substantially parallel to the centerline of the plasma lamp 34 and the substrate 60, respectively. The relative insensitivity to the separation distance is due primarily to the parallelism of the rays of ultraviolet radiation 80 reflected from reflector panels 102, 104. Likewise, the transverse position of reflector 101 can be varied slightly as long as the substrate 60 remains substantially positioned at the focal line of the parabola defined by panels 106, 108. Furthermore, it is understood by persons of ordinary skill that the inner faces 112, 114 and the inner faces 116, 118 may deviate somewhat from a mathematically-precise parabolic shape such that the shape of each need only be substantially parabolic.

Provided between respective pairs of reflector panels 102–108 are longitudinally-extending gaps 120, 122, 124 and 126 that permit paths for a flow of air to cool the plasma lamp 34 and the conduit 62. It will be appreciated that each of the pairs of reflector panels 102 and 104 and reflector panels 106 and 108 could be formed as a single or integral piece, which would eliminated at least gaps 120 and 126, respectively. Further, the quartet of reflector panels 102–108 could be formed as a single piece and all of gaps 120–126 eliminated. However, suitable cooling for the plasma lamp 34 and the conduit 62 would have to be provided in an alternative manner, such as a sufficient flow of air directed axially between the reflectors 100, 101 or by plural openings (not shown) perforating the reflector panels 102–108 in a sufficient number and with a sufficient spacing to permit a sufficient flow of air adequate to cool the plasma lamp 34 and the conduit 62.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. For example, the present invention could be used to irradiate fluids flowing within an ultraviolet-transmissive flow tube through the interior of the microwave chamber. In its broader aspects, the present invention is not limited to ultraviolet irradiation but could irradiate substrates positioned within the microwave chamber with radiation having visible wavelengths or infrared wavelengths. The invention in its broader aspects is therefore not limited to the specific details, representative apparatus and method, and illustrative examples shown and described. Accordingly, departures may be made from such details without departing from the spirit or scope of applicants' general inventive concept.

Having described the invention, we claim:

1. An ultraviolet radiation generating system for treating a coating on a substrate having a longitudinal axis, a frontside, and an opposed backside, said system comprising:

a microwave chamber having a processing space and an inlet port capable of receiving the substrate for positioning in said processing space, said microwave chamber being substantially closed to emission of microwave energy therefrom;

a longitudinally-extending plasma lamp mounted within said processing space of said microwave chamber and capable of emitting ultraviolet radiation;

a microwave generator coupled to said microwave chamber for exciting said plasma lamp to emit ultraviolet radiation, a first portion of the ultraviolet radiation irradiating the frontside of the substrate; and a longitudinally-extending first reflector mounted within said microwave chamber, said first reflector having a substantially parabolic first reflective surface with a first focal line aligned substantially collinear with said plasma lamp and oriented relative to said plasma lamp for reflecting a second portion of ultraviolet radiation as a plurality of substantially parallel rays; and a longitudinally-extending second reflector mounted within said microwave chamber, said second reflector having a substantially parabolic second reflective surface with a first focal line aligned substantially collinear with the longitudinal axis of the substrate and oriented relative to said first reflective surface for collecting and reflecting said plurality of substantially parallel rays to direct said second portion of ultraviolet radiation in a converging manner toward the backside of the substrate.

2. The ultraviolet radiation generating system of claim 1, wherein said microwave chamber further comprises:

an outlet port capable of permitting the substrate to exit said microwave chamber and an ultraviolet-transmissive conduit positioned within said microwave chamber generally between said inlet port and said outlet port, and enclosing the substrate when the substrate is positioned within said processing space.

3. The ultraviolet radiation generating system of claim 1, wherein:

said first reflector further comprises first and second reflector panels extending longitudinally within said microwave chamber, said first and second reflector panels positioned in spaced relationship with said plasma lamp.

4. The ultraviolet radiation generating system of claim 3, wherein said first and second reflector panels are positioned relative to one another for defining said first reflective surface.

5. The ultraviolet radiation generating system of claim 3, wherein said first and second reflector panels are separated by a longitudinally-extending gap that provides a flow path for a temperature-regulating gas into said processing space.

6. A method of treating a coating on a substrate positionable within a processing space of a microwave chamber having a plasma lamp mounted within the processing space and a pair of reflectors surrounding the plasma lamp, one of the pair of reflectors including a parabolic first reflective surface with a first focal line substantially collinear with the plasma lamp and the other of the pair of reflectors having a second reflective surface confronting the first reflective surface, the second reflective surface including a second focal line substantially collinear with a longitudinal axis of a substrate when the substrate is positioned within the processing space, comprising:

positioning a substrate within the processing space such that a longitudinal axis of the substrate is substantially collinear with the second focal line;

exciting the plasma lamp with microwave energy to emit ultraviolet radiation;

irradiating a frontside of the substrate with ultraviolet radiation emitted from the plasma lamp while the substrate is positioned within the processing space;

reflecting ultraviolet radiation from the first reflective surface toward the second reflective surface as a plurality of substantially parallel rays;

collecting the plurality of substantially parallel rays with the second reflective surface;

reflecting the plurality of substantially parallel rays from the second reflective surface in a converging manner toward a backside of the substrate; and removing the substrate after irradiation from the processing space.

7. The method of claim 6, wherein positioning the substrate comprises transporting the substrate through the processing space during the irradiating.

8. The method of claim 6, further comprising enclosing the substrate within an ultraviolet-transmissive conduit when the substrate is positioned within the processing space of the microwave chamber.

9. The method of claim 6, wherein irradiating the backside of the substrate comprises irradiating the backside of the substrate with a substantially uniform pattern of ultraviolet radiation about the circumference and length of the portion of the substrate within the processing space.

10. The method of claim 6, wherein irradiating the substrate alters a physical property of the coating as a result of exposure to ultraviolet radiation.

11. The ultraviolet radiation generating system of claim 3, wherein said second reflector further comprises third and fourth reflector panels extending longitudinally within said microwave chamber, said third and fourth reflector panels positioned in spaced relationship with said first and second reflector panels.

12. The ultraviolet radiation generating system of claim 11, wherein said third and fourth reflector panels are arranged relative to one another for defining said second reflective surface.

13. The ultraviolet radiation generating system of claim 11, wherein said first and second reflector panels and said third and fourth reflector panels are each separated by a longitudinally-extending gap that provides a flow path for a temperature-regulating gas into said processing space.

14. The ultraviolet generating system of claim 1, wherein said first reflective surf ace is parabolic.

15. The ultraviolet generating system of claim 1, wherein said second reflective surface is parabolic.

* * * * *